| United States Patent [19] | [11] | 4,105,851 |
| De Wald | [45] | Aug. 8, 1978 |

[54] 1,3,8-TRIMETHYLIMIDAZOPYRAZOLODIAZEPINE COMPOUNDS

[75] Inventor: Horace A. De Wald, Ann Arbor, Mich.

[73] Assignee: Parke, Davis & Company, Detroit, Mich.

[21] Appl. No.: 696,951

[22] Filed: Jun. 17, 1976

Related U.S. Application Data

[63] Continuation-in-part of Ser. No. 611,042, Sep. 8, 1975, abandoned.

[51] Int. Cl.$^2$ ............................................. C07D 487/14
[52] U.S. Cl. ................................. 548/324; 424/273 R; 424/273 P; 548/336
[58] Field of Search ......................... 260/309, 310 R; 548/324

[56] References Cited

U.S. PATENT DOCUMENTS

| 3,709,898 | 1/1973 | Hester ................................ 260/308 R |
| 3,763,179 | 10/1973 | Gall ..................................... 260/309 |
| 3,770,762 | 11/1973 | Butler ................................ 260/310 R |
| 3,823,157 | 7/1974 | De Wald .......................... 260/310 R |
| 3,849,434 | 11/1974 | Coffen et al. ..................... 260/308 R |
| 3,852,461 | 12/1974 | Hester et al. ......................... 260/309 |

*Primary Examiner*—Natalie Trousof
*Attorney, Agent, or Firm*—David B. Ehrlinger; Stephen Raines; Frank S. Chow

[57] ABSTRACT

4-Aryl-1,6-dihydro-1,3,8-trimethylimidazo[1,2-a]-pyrazolo[4,3-f][1,4]diazepines; and acid-addition salts. The aryl group is o-fluorophenyl or o-chlorophenyl. The compounds are pharmacological agents, especially anticonvulsant and antianxiety agents. They can be produced by reacting an aryl-(2-hydroxymethyl)-imidazol-1-yl-1,3-dimethylpyrazol-4-ylmethanone hydrocarbon sulfonate ester with ammonia in the presence of iodide.

3 Claims, No Drawings

1,3,8-TRIMETHYLIMIDAZOPYRAZOLODIAZEPINE COMPOUNDS

This application is a Continuation in part of application Ser. No. 611,042 filed Sept. 8, 1975, now abandoned.

SUMMARY AND DETAILED DESCRIPTION

The present invention relates to new diazepine compounds. More particularly, the invention relates to certain new 4-aryl-1,6-dihydro-1,3,8-trimethylimidazo[1,2-a]pyrazolo[4,3-f][1,4]diazepine compounds; to salts thereof; and to a method for the production of the foregoing compounds.

In the forms of their free bases, the compounds of the invention can be represented by the formula

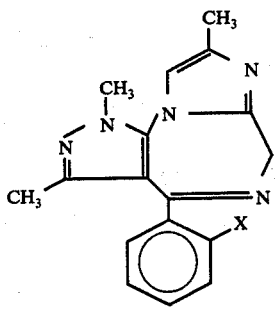

I where X represents fluorine or chlorine.

The compounds of the invention can be produced by reacting an aryl-(2-hydroxymethyl)imidazol-1-yl-1,3-dimethylpyrazol-4-ylmethanone hydrocarbon sulfonate ester compound of the formula

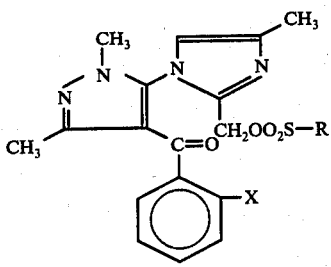

II with ammonia in the presence of iodide; where R is lower alkyl of from one to four carbon atoms, aryl or trifluoromethyl, and X is as defined before.

The R group is preferably methyl; aryl is preferably phenyl or substituted phenyl such as halophenyl, alkylphenyl, alkoxyphenyl or nitrophenyl. For the reaction any soluble metal iodide may be used, especially an alkali metal iodide, which is preferred, or an alkaline earth metal iodide. Catalytic to equivalent amounts of iodide may be used; a large excess of ammonia is preferred. Liquid ammonia may be used as a solvent or one may use an added solvent such as a lower alkanol (for example, methanol or ethanol), a chlorinated hydrocarbon (for example, dichloromethane or chloroform), an ether (for example, tetrahydrofuran or dioxane), and mixtures of these solvents. The reaction conditions may be varied widely. The reaction can be carried out at temperatures in the range from about −20° C. to about 80° C. and is complete within periods ranging from about 2 to 24 hours. It is preferable to start the reaction at the lower temperature and then, after 1 to 2 hours, to allow the reaction mixture to warm to room temperature. The product is isolated as the free base or as an acid-addition salt following adjustment of the pH as necessary.

The aryl-(2-hydroxymethyl)imidazol-1-yl-1,3-dimethylpyrazol-4-ylmethanone hydrocarbon sulfonate ester compounds employed as starting materials in the foregoing process can be obtained by reacting an aryl-(2-hydroxymethyl)imidazol-1-yl-1,3-dimethylpyrazol-4-ylmethanone with hydrocarbon sulfonyl chloride in the presence of a tertiary amine. These procedures are illustrated in greater detail hereinafter.

The free bases of the invention form acid-addition salts with any of a variety of organic and inorganic acids. Pharmaceutically-acceptable acid-addition salts are formed with such acids as hydrochloric, hydrobromic, sulfuric, nitric, phosphoric, acetic, citric, tartaric, succinic, salicylic, maleic, malic, lactic, gluconic, and pamoic acids. In most cases salts with one equivalent of a mineral acid or a strong organic acid are stable chemical derivatives. The free bases and their salt forms are interconvertible by adjustment of the pH. The free bases are produced by basification and the acid-addition salts are produced by acidification. They differ in solubility properties but, in general, are otherwise equivalent for the purposes of the invention.

The compounds of the invention are new chemical compounds that are useful as pharmacological agents. They exert anticonvulsant and antianxiety effects while being only minimally depressive upon the central nervous system. The anticonvulsant effect is shown by their ability to prevent the occurrence of convulsions in animals following the administration of pentamethylenetetrazole. The antianxiety effect is shown by their ability to overcome inhibited behavior in animals placed in an anxiety-producing situation.

The anticonvulsant activity of the compounds of the invention is measured in a standard test in which each of a group of 5 rats is given a measured oral dose of a test compound, dissolved in water or suspended with acacia, followed 30 minutes later by a subcutaneous dose of 93 mg./kg. of pentamethylenetetrazole. This quantity of pentamethylenetetrazole quickly produces convulsions in 98–100% of untreated control rats. The treated animals are then observed visually for 30 minutes following administration of pentamethylenetetrazole, and anticonvulsive activity is judged by noting the time of onset and severity of clonic convulsive seizures and the number of animals completely protected from convulsions. The activity of a test compound at each dosage level is rated as follows: 4+, protection of all 5 rats; 3+, protection of 3 or 4 rats; 2+, protection of one or 2 rats; 1+, delay in onset; 0, no effect.

Some results obtained for compounds of the present invention when tested by the foregoing procedure are as follows: X representing fluorine, 4+ at 8 to 64 mg./kg.; X representing chlorine, 3+–4+ at 8 to 64 mg./kg.

The antianxiety activity of the compounds of the invention is determined in a test that measures food consumption by rats that have been placed in an anxietyproducing situation. In this test, newly arrived Holtzman male albino rats are allowed to adjust to the laboratory environment for at least three days before testing. When tested, the animals are experimentally naive, are under no condition of dietary deprivation, and weigh about 230 grams. After adjustment to the normal laboratory environment, each of a group of 8 rats is given a measured dose of test compound, dissolved in water or suspended in 0.2% aqueous methylcellulose, by oral intubation and is immediately placed in an individual metabolism cage. A 30-minute period is allowed for absorption of the test compound. Each animal is then given access to a milk preparation in a graduated and calibrated tube. The preparation consists of one part sweetened condensed milk and two parts water. The total milk intake of each animal after 1 and 2 hours is recorded and compared with that of a group of 8 untreated control animals. The animals are also observed for any gross behavioral signs and symptoms. Greater than normal ingestion of milk by the treated animals is regarded as an indication that the test compound, by acting upon the inhibitory brain systems, has suppressed the natural tendency of rodents to become immobilized in a novel, anxiety-producing situation, as represented in the test by the isolation of the metabolism cage. A given dose of test compound is considered active if it causes a mean amount of ingestion greater than 5.0 ml. per animal at the end of the first hour of the test. During this same period, the untreated controls normally consume between 2.0 and 4.0 ml. of milk.

Some activities of compounds of the present invention, as determined by the foregoing procedure, are as follows in which the first value given is the volume of milk ingested by the end of the first hour of the test: X = chlorine, 6.2 ml. at 40 mg./kg.; 9.9 ml. at 20 mg./kg.; 8.6 ml. at 10 mg./kg.; X = fluorine, 5.8 at 5 mg./kg.; 8.0 ml. at 2.5 mg./kg.; 6.4 ml. at 1.25 mg./kg. The pharmacological agents diazepam and chlordiazepoxide, which are known to be clinically useful for the treatment of anxiety states, are also active in this test procedure. The demonstration of activity for diazepam and chlordiazepoxide indicates the validity of the test procedure for determining antianxiety activity.

The compounds of the invention are preferably administered orally, as indicated above, although parenteral administration can also be used. They can be combined with either a solid or liquid carrier of diluent and made available in varying amounts in such pharmaceutical forms as tablets, capsules, powders, and aqueous and nonaqueous suspensions and solutions.

The invention is illustrated by the following examples.

EXAMPLE 1

A solution of 5.0 g. of (2-chlorophenyl)-[5-[2-(hydroxymethyl)-4-methyl-1H-imidazol-1-yl]-1,3-dimethyl-1H-pyrazol-4-yl]methanone and 2.5 ml. of triethylamine in 75 ml. of methylene dichloride is cooled to −5° C. and treated dropwise with 2 g. of methanesulfonyl chloride. The reaction mixture is stirred at −5° C. for another hour, then refrigerated overnight (5° C.). The mixture is washed first with water and then with saturated sodium bicarbonate solution. The solution is dried over magnesium sulphate and evaporated in vacuo. The product is (2-chlorophenyl)-[5-[2-(hydroxymethyl)-4-methyl-1H-imidazol-1-yl]-1,3-dimethyl-1H-pyrazol-4-yl]-methanone, methane sulfonate ester. The product is dissolved in 75 ml. of tetrahydrofuran and cooled to −20° C. The solution is treated with 5 g. of potassium iodide and about 15 ml. of liquid ammonia is introduced. The mixture is stirred at −20° C. for 1-2 hours and then allowed to warm to room temperature overnight. The reaction mixture is evaporated in vacuo. The residual product is 4-(2-chlorophenyl)-1,6-dihydro-1,3,8-trimethylimidazo[1,2-a]-pyrazolo[4,3-f][1,4]diazepine; m.p. 150–153° C. after washing (dichloromethane/water), drying, concentration to dryness, percolation over a neutral alumina column in ethyl acetate, reconcentration to dryness and recrystallization from ether.

To obtain the hydrochloride salt, the free base product is dissolved in tetrahydrofuran and the solution is treated with an excess of a saturated solution of hydrogen chloride in 2-propanol and diluted with ether to turbidity. The resulting monohydrochloride salt which precipitates is collected and dried; m.p. 275° C. (dec.).

EXAMPLE 2

Following the procedure of the previous example but starting instead with (2-fluorophenyl)-[5-[2-(hydroxymethyl)-4-methyl-1H-imidazol-1-yl]-1,3-dimethyl-1H-pyrazol-4-yl]methanone (3.3 g.) and with 1.8 g. of methanesulfonyl chloride, the product is (2-fluorophenyl)-[5-[2-(hydroxymethyl)-4-methyl-1H-imidazol-1-yl]-1,3-dimethyl-1H-pyrazol-4-yl]methanone, methanesulfonate ester. Also, following the same procedure, treating the methanesulfonate ester product with excess liquid ammonia in tetrahydrofuran in the presence of potassium iodide, the product is 4-(2-fluorophenyl)-1,6-dihydro-1,3,8-trimethylimidazo[1,2-a]pyrazolo[4,3-f][1,4]-diazepine; m.p. 153°–154° C. after crystallization from ethyl acetate-petroleum ether.

Starting Materials

Starting materials for the Examples can be prepared by the procedures under the following headings (a) and (b):

Aroyl-(5-imidazol-1-yl)-pyrazol-4-yl methanones (a-1) A mixture of 27 g. of 5-chloro-4-(o-chlorobenzoyl)-1,3-dimethylpyrazole (U.S. Pat. No. 3,558,605) and 10 g. of 4-methylimidazole in 150 ml. of dimethylformamide is treated portionwise with 5 g. of sodium hydride (50% dispersion in mineral oil) under nitrogen. The mixture is stirred and heated under nitrogen gas at 90°–100° C. for 4 hours. The mixture is filtered and evaporated in vacuo. The residue is dissolved in ethyl acetate and extracted with two 150-ml. portions of N HCl. The combined aqueous extract is made basic with concentrated NH$_4$OH and extracted with dichloromethane. The organic extract is washed with brine, dried over MgSO$_4$ and evaporated in vacuo. The product is (2-chlorophenyl)-[5-[4-(methyl)-1H-imidazol-1-yl]-1,3-dimethyl-1H-pyrazol-4-yl]methanone; m.p. 125°–128° C. after crystallization from ether. (a-2) From 25 g. of 5-chloro-1,3-dimethyl-4-(o-fluorobenzoyl)-pyrazole (U.S. Pat. No. 3,558,605), 9 g. of 4-methylimidazole and 5.5 g. of 50% sodium hydride in 200 ml. of dimethylformamide, following the procedure of (a-1), there is obtained 18 g. of (2-fluorophenyl)-[5-[4-(methyl)-1H-imidazol-1-yl]-1,3-dimethyl-1H-pyrazol-4-yl]-methanone; m.p. 136–139° C. from ether.

Aroyl-[5-[2-(hydroxymethylimidazol-1-yl)-pyrazol-4-yl]-methanones (b-1) A mixture of 20 g. of (2-chlorophenyl)-[5-[4-(methyl)-1H-imidazol-1-yl]-1,3-dimethyl-1H-pyrazol-4-yl]-methanone and 60 ml. of 37% aqueous formaldehyde is stirred and heated under reflux for 40 hours and is evaporated in vacuo. The residue is dissolved in warm ethyl acetate and the solution washed with water; then it is extracted with 300 ml. of N HCl. The aqueous HCl extract is made strongly basic with concentrated NH₄OH and extracted with dichloromethane. The organic extracts are washed with brine, dried over MgSO₄ and evaporated in vacuo. The residual product is (2-chlorophenyl)-[5-[2-(hydroxymethyl)-4-methyl-1H-imidazol-1yl]-1,3-dimethyl-1H-pyrazol-4-yl]methanone; m.p. 195-197° C. from ethyl acetate.

(b-2) From 18 g. of (2-fluorophenyl)-[5-[4-(methyl)-1H-imidazol-1-yl]-1,3-dimethyl-1H-pyrazol-4-yl]methanone and 50 ml. of 37% formalin, following the procedure of (b-1), the product is (2-fluorophenyl)-5-[2-(hydroxymethyl)-4-methyl-1H-imidazol-1-yl]-1,3-dimethyl-1H-pyrazol-4-yl]-methanone; m.p. 185°–186° C. from ethyl acetate.

CLAIMS:

1. A compound of the formula

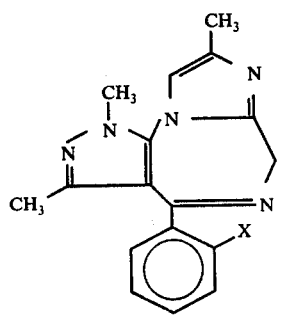

and acid-addition salts thereof; where X is fluorine or chlorine.

2. A compound according to claim 1 which is 4-(2-chlorophenyl)-1,6-dihydro-1,3,8-trimethylimidazo[1,2-a]pyrazolo[4,3-f][1,4]diazepine.

3. A compound according to claim 1 which is 4-(2-fluoropheyl)-1,6-dihydro-1,3,8-trimethylimidazo[1,2-a]pyrazolo[4,3-f][1,4]diazepine.

* * * * *